United States Patent [19]
Lasseur et al.

[11] Patent Number: 6,077,548
[45] Date of Patent: Jun. 20, 2000

[54] ORGANIC WASTE PROCESSING METHOD, AND USES THEREOF

[75] Inventors: Christophe Andre Antoine Lasseur, Wassenaar, Netherlands; Jacques Ernest Nicolas Richalet, Louveciennes, France; Willy Henry Verstraete, Wondelgem, Belgium

[73] Assignee: Agence Spatiale Europeenne, Paris, France

[21] Appl. No.: 09/125,627

[22] PCT Filed: Feb. 20, 1997

[86] PCT No.: PCT/FR97/00316

§ 371 Date: Dec. 7, 1998

§ 102(e) Date: Dec. 7, 1998

[87] PCT Pub. No.: WO97/31120

PCT Pub. Date: Aug. 28, 1997

[30] Foreign Application Priority Data

Feb. 21, 1996 [FR] France .................................. 96 02131

[51] Int. Cl.[7] ....................................................... A23B 4/12
[52] U.S. Cl. ................... 426/7; 426/69; 435/268; 435/290.1; 435/292.1; 435/303.2
[58] Field of Search .................... 426/7, 61, 69, 426/392; 210/601, 603, 605, 606, 607, 609, 613, 623, 630, 767, 175, 252; 49/646 LS; 435/268, 264, 290.1, 290.4, 292.1, 294.1, 303.2

[56] References Cited

U.S. PATENT DOCUMENTS

| | | | |
|---|---|---|---|
| 3,930,998 | 1/1976 | Knopp et al. | 210/5 |
| 4,277,342 | 7/1981 | Hayes et al. | 210/609 |
| 4,919,813 | 4/1990 | Weaver | 210/603 |
| 5,250,427 | 10/1993 | Weaver et al. | 435/42 |

FOREIGN PATENT DOCUMENTS

| | | |
|---|---|---|
| 2477522 | 9/1981 | France . |
| 8400038 | 1/1984 | WIPO . |
| 9304988 | 3/1993 | WIPO . |

OTHER PUBLICATIONS

Database WPI, Section Ch, Week 7832, Derwent Pub. Ltd., London, GB, Cl. C04, AN 78–57463A, Jul. 4, 1978.
Database WPI, Section Ch, Week 9317, Derwent Pub. Ltd., London, GB, Cl. D13, AN 93–141626, May 7, 1992.
Database WPI, Section Ch, Week 9320, Derwent Pub. Ltd., London, GB, Cl. D15, AN 93–163777, Apr. 20, 1993.
Meregeay et al., Proceed. of the 3rd EU Symp. on Space Thermal Con. & Life Supt. Syst., Oct. 3–8, 1988.

*Primary Examiner*—Keith D. Hendricks
*Attorney, Agent, or Firm*—Sughrue, Mion, Zinn, Macpeak & Seas, PLLC

[57] ABSTRACT

The present invention relates to an open circuit organic waste treatment method, to a plant for carrying out the method, and to applications of that method. The treatment method is characterized in that it comprises the following steps: a) collecting the waste; b) introducing the waste into a first reactor without prior sterilisation; c) decomposing the waste in said first reactor using mesophilic or thermophilic anaerobic bacteria; d) recovering the liquid effluent resulting from said decomposition and transferring it to a second reactor containing heterotrophic or photoheterotrophic bacteria; e) using the heterotrophic or photoheterotrophic bacteria to produce an edible biomass constituted by said bacteria; and f) recovering and packaging the biomass produced. A particular application of the method is that of recycling organic waste of animal origin such as liquid manure or sludge originating from water purification.

17 Claims, 1 Drawing Sheet

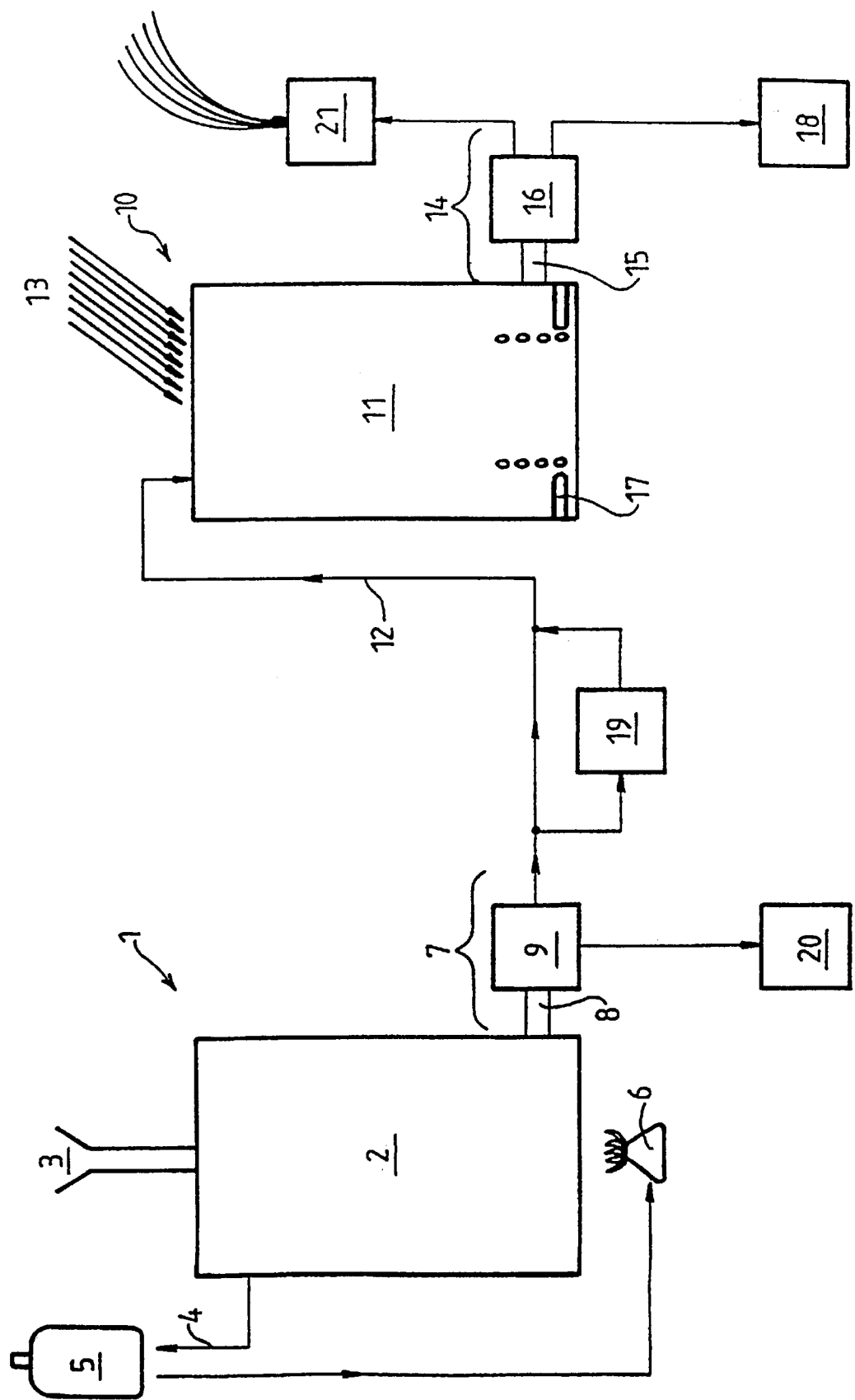

6,077,548

ORGANIC WASTE PROCESSING METHOD, AND USES THEREOF

This application is a 371 of PCT/FR97/00316, filed Feb. 20, 1997.

1. Field of the Invention

The present invention relates to an organic waste treatment method, to a plant for carrying out the method, and to applications of that method.

2. Background of the Invention

The term "environment" has grown in importance in recent years. Hygiene and safety concerns, and those concerning the protection of man, nature, and ecological balances have now been added to aesthetic concerns (indiscriminate dumping, visible pollution).

Faced with the increasing amount of waste which has to be eliminated, regulations in a certain number of European countries regarding environmental protection have been aimed at reducing the quantity of waste discharged without being commercially exploited, and discharges must in the future be limited to ultimate residues which have been rendered appropriately inert. Thus it will be permitted to discharge only waste waste, after all forms of adding value have been exploited.

Thus there is a real need to develop technologies which can enable waste to be recycled in an optimum manner and whatever its origin and nature (household, agricultural, industrial waste . . . ). Such technologies must satisfy the economic principles applicable to all production and must result in products with a real value in a variety of markets at satisfactory production costs. In this regard, the energy cost of recycling must be as low as possible.

While organic waste of animal origin, in particular excreta produced from intensive livestock farming, can spontaneously decompose in contrast to other waste (inorganic waste, synthesised organic macromolecules) which have to be treated, such waste causes serious environmental problems because of the very high volumes thereof, the nuisance caused by it (for example nauseating smells) and the polluting nature of the high concentrations of nitrogen-containing compounds resulting from its decomposition.

In another field, stations for treating and purifying sewage are confronted with problems of storing and eliminating the sludge produced during sewage purification. The volume of which sludge is increasing with time and for which there is no possibility of exploitation.

Incineration has been proposed to treat organic waste. However, incineration has a number of disadvantages: it is expensive as regards both investment and use, and fumes and gas are emitted which require further treatment with a corresponding economic cost. Further, the residues from incineration are of low commercial value.

Composting methods are also known in which the waste is anaerobically decomposed by bacteria and which result in the formation of compost which is used by farmers as fertilisers. These methods, however, are unsatisfactory as the duration of the waste treatment is long (20 days on average are required to obtain compost) and the compost obtained, which is low in nutrients (nitrogen, phosphorous), is a fertiliser of mediocre quality. Further, composting is accompanied by the emission of nauseating odours which mean that the gas emitted must undergo a specific treatment, or substances for reducing production of that gas must be added.

Methods for biologically treating organic waste which generally aim to reduce the amount of toxic products in the waste, in particular nitrogen, are also known, with the intention of re-introducing it into the anabolic circuit.

The applicant has thus aimed to provide a process for treating organic waste, whether it be waste of animal origin or waste from the purification of water or the like, which ensures optimum quantitative and qualitative exploitation of the waste, in a small number of days, without producing toxic products and with low operating costs.

Further, methods aimed at solving the problem of producing food, water, and oxygen on board space ships from waste produced by the astronauts with a view to reducing the quantities of food, water, and oxygen to be carried on lift-off and to ensure biological autonomy of the crew have been proposed (MERGEAY et al., Proceedings of the $3^{rd}$ Symposium on Space Thermal Control & Life Support Systems, Noordwijk, THE NETHERLANDS, Oct. 3–6, 1988). Such methods constitute an artificial ecosystem comprising four axenic compartments colonised by micro-organisms, the principal functions of which represent different stages in the ecosystem (waste liquefaction, nitrification, biosynthesis), and a fifth compartment termed the "consumer" compartment represented by the crew. That ecosystem was designed to operate in a closed circuit under anoxygenic conditions to limit oxygen consumption, using all of the products present in the circuit, with no possibility of any one of them leaving at any time. This means that such an ecosystem could not be used to recycle organic waste on earth because of the technical and economic constraints it would impose.

SUMMARY OF THE INVENTION

The applicant has discovered that, to solve a different problem, namely that of exploiting organic waste, techniques proposed for producing a system for producing, food, water, and oxygen in a closed circuit can surprisingly be adapted to produce an open system for treating waste on an industrial scale and to produce an edible biomass with a high nutritional value for the production of animal feeds, for the production of readily exploitable fuel gas, and finally for the production of products which can be used as fertilisers.

Thus the present invention provides an open circuit organic waste treatment method, characterized in that it comprises the following steps:

a) collecting the waste;

b) introducing the waste into a first reactor without prior sterilisation;

c) decomposing the waste in said first reactor using mesophilic or thermophilic anaerobic bacteria;

d) recovering the liquid effluent resulting from said decomposition and transferring it to a second reactor containing heterotrophic or photoheterotrophic bacteria;

e) using the heterotrophic or photoheterotrophic bacteria to produce an edible biomass constituted by said bacteria; and f) recovering and packaging the biomass produced.

Within the context of the present invention, the terms:

"mesophilic anaerobic bacteria" means bacteria which can develop in the absence of oxygen and at temperatures in the range 20° C. to 40° C.;

"thermophilic anaerobic bacteria" means bacteria which can develop in the absence of oxygen and at temperatures of over 45° C. and possibly up to 85° C.;

"heterotrophic bacteria" means bacteria which can assimilate organic carbon-containing sources using oxygen as an energy source which consequently can develop on such sources; and "photoheterotrophic bacteria" means bacteria which are also capable of developing on carbon-containing sources but using light as the energy source.

In a first preferred implementation of the treatment method of the invention, the mesophilic or thermophilic anaerobic bacteria which decompose the waste are a mixture of proteolytic, saccharolytic and cellulolytic bacteria, simultaneously hydrolyse the different biological polymers (proteins, carbohydrates, DNA, RNA, lipids, cellulose, . . . ) forming part of the constitution of the waste to small carbon-containing and nitrogen-containing compounds which can be assimilated by the heterotrophic or photoheterotrophic bacteria present in the second reactor.

These small carbon-containing and nitrogen-containing compounds are mainly volatile fatty acids (acetic acid, valeric acid, butyric acid, isobutyric acid, propionic acid, caproic acid, . . . ), amines, urea, ethanol and ammonia.

Advantageously, the mesophilic or thermophilic anaerobic bacteria which decompose the waste are commensal animal intestine bacteria.

In a preferred implementation of the treatment method of the invention, waste decomposition is carried out using thermophilic anaerobic bacteria at a temperature in the range 45° C. to 80° C., preferably in the range 55° C. to 70° C. Using such a temperature eliminates pathogenic germs such as bacteria, yeasts, protozoa, or viruses which may be present in the waste when it is introduced into the first reactor, while allowing the thermophilic bacteria for decomposing the waste to develop and carry out their function.

In accordance with the invention, waste decomposition is carried out over a period which is sufficient to obtain decomposition of the proteins, polysaccharides, and lipids present in the waste to a degree of over 80%. This decomposition results in liquefaction of the waste and in production of an effluent which comprises a liquid phase and a solid phase formed by particles suspended in the liquid phase.

In a further preferred variation of the treatment method of the invention, recovery of the effluent resulting from the waste decomposition comprises a step for separating the liquid and solid phases of said effluent.

Separation is preferably carried out by filtering or screening.

In a still further preferred variation of the treatment method of the invention, the heterotrophic or photoheterotrophic bacteria which produce the edible biomass are from the Rhodospirillaceae family. These bacteria can develop on a large number of carbon-containing sources, in particular on the volatile fatty acids present in the liquid effluent from waste decomposition, both for aerobiosis in the absence of light (respiration) and for anaerobiosis in the presence of light (photosynthesis), thus enabling the edible biomass to be produced by bacterial growth, under conditions both of aerobiosis and of anaerobiosis.

Preferred bacteria of the Rhodospirillaceae family are bacteria from the genus Rhodobacter such as *Rhodobacter capsulatus* and/or from the genus Rhodospirillum such as *Rhodospirillum rubrum*.

In accordance with the invention, the edible biomass is advantageously produced by heterotrophy and aerobiosis.

In a further preferred variation of the treatment method of the invention, recovery of the edible biomass comprises a step for separating this biomass from the liquid effluent in which it is immersed.

This separation is preferably by flotation.

In a yet still further preferred variation of the treatment method of the invention, it further comprises removing the fuel gases ($CH_4$, $H_2$, . . . ) produced during waste decomposition to exploit them by combustion.

Advantageously, gas combustion is used to heat the first reactor.

The open circuit organic waste treatment method of the invention also comprises composting the residual solid matter from waste decomposition to upgrade them in the form of compost.

In addition to solving environmental problems caused by an accumulation of organic waste, such a method has the advantage of giving value to the waste by enabling it to be transformed into an edible biomass with a high nutritional value which can be used in animal feeds, and also into a gas which is readily valorisable by combustion and into fertilising products, without producing toxic residues, and at a cost which is compatible with industrial requirements.

The invention also provides a plant for carrying out the open circuit organic waste treatment method defined above, characterized in that it comprises:

a) a first reactor for decomposing waste using mesophilic or thermophilic anaerobic bacteria, comprising a vessel provided with means for supplying the waste and means for recovering liquid effluent resulting from that decomposition;

b) a second reactor using heterotrophic or photoheterotrophic bacteria to produce an edible biomass constituted by said bacteria, said second reactor comprising a vessel provided with means for recovering the biomass produced;

c) means for transferring said effluent from the first reactor to the second reactor; and d) means for packaging said biomass.

In a first preferred variation of the plant of the invention, the vessel for the first reactor is provided with heating means and/or means for removing the gas released in said vessel during waste decomposition.

Advantageously, the vessel for the first reactor is provided both with heating means and with means for removing the gas released during waste decomposition, and the heating means comprises a heating system supplied by the means for removing gas, directly or via a storage means.

In a further preferred variation of the plant of the invention, the means for recovering liquid effluent resulting from waste decomposition comprises means for evacuating that effluent from the vessel for the first reactor and means for separating the phases to separate its liquid and solid phase constituents.

In a further preferred variation of the plant of the invention, the vessel for the second reactor is provided with lighting or aeration means.

In a first advantageous embodiment of the plant of the invention, the vessel for the second reactor is partly or completely constructed from a transparent material and the lighting means comprises a source of natural light (sunlight) or artificial light located outside said vessel.

In a further advantageous embodiment of this plant, the lighting means for the second reactor vessel comprises an artificial light source located inside said vessel.

In a still further preferred variation of the plant of the invention, the means for recovering edible biomass comprises means for evacuating said biomass from the second reactor vessel and phase separator means for separating the biomass from the liquid effluent in which it is immersed.

Advantageously, the edible biomass packaging means comprises draining means and/or sterilising means and/or dehydrating means.

In a particularly preferred embodiment of the plant of the invention, it also comprises a composting unit for exploiting, in the form of compost, the residual solid material from decomposing the waste.

The present invention also encompasses the application of the open circuit organic waste treatment method as defined above to recycling animal waste such as excreta present in farm animal bedding (from pigs, ruminants, horses, poultry, . . . ), and in liquid manure.

The present invention also encompasses the application of this recycling method to sludge originating from water purification.

The present invention still further encompasses the application of the same method to the production of animal feed.

Further characteristics and advantages of the invention will become apparent from the remainder of the description which is made with reference to the accompanying drawing.

BRIEF DESCRIPTION OF THE DRAWING

The sole FIGURE is a block diagram of a plant of the invention, and also to examples of the invention applied to the treatment of liquid pig manure.

The remainder of the description is, of course, given by way of illustration only and is in no way limiting.

DESCRIPTION OF THE PREFERRED EMBODIMENT

We shall now refer to the accompanying figure.

A plant in accordance with the invention—which may be on the site where the waste is produced or off-site—comprises a first reactor (1) comprising a vessel (2) for receiving a set volume of waste to decompose it using mesophilic or thermophilic anaerobic bacteria. Vessel (2) is provided with means (3) for supplying the waste from its production zone or from a receiving and storage pit; the means may be of gravity, hydraulic, mechanical, or other type.

Vessel (2) can be a pit or reservoir type open vessel and can optionally be equipped with movable closure means. It can also be a closed digester or tank type vessel.

Depending on the nature of the waste to be treated and the conditions under which it is decomposed (temperature, pH, residence time of waste in the vessel, . . . ) it is accompanied by a greater or lesser production of fuel gas ($CH_4$, $H_2$, . . . ). Further, the first reactor (1) can advantageously comprise means (4) for removing the fuel gas released in the vessel (2) during waste decomposition to exploit it by combustion, either immediate or delayed, in the latter case guiding the removed gas to a storage means (5) comprising, for example, compressors or liquefiers, and bottles.

In accordance with the invention, the waste decomposition can be mesophilic or thermophilic, i.e., it can be carried out at temperatures which are in the range 20° C. to 80° C. Depending on the temperature selected to carry out this decomposition, it may be necessary or advantageous to provide vessel (2) for the first reactor (1) with heating means (6) to heat the waste to this temperature and to keep it at this temperature.

The heating means (6) which may, for example, comprise one or more coils for circulating a heat transfer fluid such as hot water connected to a heat source (a boiler, for example) can be supplied exclusively by a source outside the plant (electrical heating, fuel heating, gas heating, . . . ).

However, when the vessel (2) for the first reactor (1) is also provided with means for removing the gas released during waste decomposition, it may be extremely advantageous to use this gas as the energy source for heating the vessel.

In this case, the means (6) for heating vessel (2) comprises, for example, a first heating system supplied by an energy source which is external to the plant and a second heating system which is independent of the first and has one or more burners supplied by the means (4) for removing the gas present in vessel (2), directly or via a gas storage means (5). In a variation, the means (6) for heating vessel (2) comprises a single heating system provided with two inlets, the first being connected to an energy source which is external to the plant and the second being supplied by the means (4) for removing gas from the vessel (2) and/or its storage means (5).

Advantageously, vessel (2) of the first reactor (1) is thermally insulated and the heating means (6) is provided with a thermostatic device to keep the waste at a constant temperature.

Vessel (2) of first reactor (1) can also include stirring means, which can be permanent or intermittent, to homogenize the waste and to encourage contact with the bacteria.

In accordance with the invention, vessel (2) of the first reactor (1) is provided with means (7) for recovering the liquid effluent resulting from waste decomposition.

These recovery means (7) comprise means (8) for evacuating effluent from vessel (2) which can, for example, be constituted by an apparatus ensuring partial or complete emptying of that vessel (2), by pumping, siphoning, runoff, etc. The means also comprises phase separator means (9) connected to the evacuation means (8) to separate the liquid and solid phases of the effluent and thus to free it of the suspended solid material contained therein. This phase separation can be effected using any conventional method for separating a liquid phase and a solid phase: filtering or screening through a filter or a screen provided with suitable openings (ideally, 150 μm or less), by sedimentation in a settling tank, by flotation in flotation equipment, or by centrifuging in a centrifuge.

As can be seen in the figure, the plant of the invention includes a second reactor (10) which comprises a vessel (11) to receive, from the first reactor (1) or from an intermediate storage tank (19), a set volume of effluent for producing the edible biomass using heterotrophic or photoheterotrophic bacteria. To this end, the plant of the invention comprises effluent transfer means (12) such as an outflow channel, one end of which opens into the first reactor (1) or into the intermediate storage tank (19), and the other end of which opens into the second reactor (10).

In accordance with the invention, the edible biomass is produced by bacterial growth, either by heterotrophy or by photoheterotrophy. The heterotrophic technique necessitates supplying oxygen to the bacteria and thus implies conditions for aerobiosis. The photoheterotrophic technique necessitates supplying light and implies conditions for anaerobiosis.

The vessel (11) of the second reactor can be designed to enable it to be used in only one of the two synthesis techniques. Advantageously, it can also be designed to enable the edible biomass to be produced by heterotrophy and aerobiosis or by photoheterotrophy and anaerobiosis, depending on the waste to be treated, on weather conditions, or on economic conditions, etc.. Thus it may be an open vessel such as a reservoir, provided with a movable system allowing it to be hermetically sealed for anaerobiosis or, in contrast, it may be a hermetically sealed vessel such as a tank provided with aeration means (17) for aerobiosis.

Such aeration means (17) advantageously comprise diffuser type means, placed at the bottom of the vessel to supply it with oxygen at a pressure sufficient to overcome the hydrostatic pressure existing at the diffuser.

This vessel is also provided with lighting means (13) suitable to supply light to the bacteria when the edible biomass is produced by photoheterotrophy. The vessel can be partly or completely constructed from a transparent material such as glass and can be equipped with an external lighting system comprising a set of lamps suitably distributed over its external surface. In a variation, vessel (11), also partly or completely constructed from a transparent material, can be illuminated by sunlight directly or via mirrors which can capture sunlight and apply it to the external surface. In a still further variation, the interior rather than the exterior of vessel (11) can be provided with an artificial lighting system. Of course, it is also possible to provide a lighting system using two light sources, one natural and the other artificial, simultaneously or alternately. In all cases, it may be advantageous to provide vessel (11) with apparatus enabling the intensity of lighting supplied to the bacteria to be adjusted.

Further, to compensate for the heat released when the lighting system or systems are operating and to maintain the internal temperature of the vessel (11) at a constant value, the vessel can advantageously be provided with a thermal insulation system, or even a cooling system circulating a cooling fluid in a heat exchanger.

Vessel (11) of the second reactor (10) can also contain a stirring or agitation device, which may operate intermittently or continuously.

In accordance with the invention, vessel (11) of the second reactor (10) is provided with means (14) for recovering the biomass produced in the vessel. These recovery means (14) comprise means for evacuating all or part of the contents of vessel (11) and means for separating the liquid effluent in which it is immersed. This separation can be effected by filtering, for example using an ultrafiltration membrane, by sedimentation using a parallel flow settling tank, or by flotation in flotation equipment.

The second reactor (10) comprises means (18) for packaging the biomass. The term "packaging" means any operation aimed at putting the biomass into the desired form (bricks, cakes, lumps, pastes, liquids, . . . ) and/or in a presentation suitable for transport (placed in containers, for example) or for its marketing. Thus this packaging means (18) can comprise means for draining the biomass, and thus for concentrating it, means for sterilising it, and means for dehydrating it to exploit it in the form of a dry product.

The accompanying figure shows that the plant of the invention also comprises a composting unit (20) for exploiting residual solid material from the waste decomposition in the form of compost, and an apparatus (21) for storing residual effluent with a view to spreading it subsequently on agricultural land.

The solid material can be composted in any plant which is conventionally used for composting waste. In accordance with the invention, however, it is preferable to accelerate composting of the solid material using forced aeration which, since it constitutes a thermophilic biological process, dehydrates it, stabilises it (suppressing bad odours), and destroys pathogenic germs which it may contain. To this end, the composting unit (20) comprises one or more silos which are equipped with one or more ventilation systems to ensure permanent aeration.

The plant of the invention may include a monitoring and control system comprising a central computer type unit or a programmable switch receiving information relating to various parameters (temperature, pH, light intensity, pressure, flow rate, valve position, . . . ) via sensors and/or probes suitably distributed about the plant, and comprising outlets connected to various control means to correct the values of these parameters if necessary and to optimise the operating conditions for the waste treatment method.

The plant of the invention can be designed to treat the waste in batches, or semi-continuously and/or continuously.

To carry out the method of the invention, waste to be treated is introduced into vessel (2) of the first reactor (1) to be decomposed therein. This decomposition is advantageously carried out by a population of anaerobic bacteria combining proteolytic, saccharolytic, and cellulolytic bacteria, so as to obtain simultaneous hydrolysis of the different polymers (proteins, carbohydrates, DNA, RNA, lipids, cellulose, . . . ) present in the waste.

Commensal bacteria from animal intestines constitute such populations. They are also generally capable of tolerating temperatures of over 45° C. Thus in the case of waste constituted by animal excreta such as liquid manure, mesophilic or thermophilic decomposition of the waste is advantageously carried out by the bacteria which are naturally present in this waste.

For other waste, it may be necessary or even advantageous to introduce into vessel (2) of the first reactor (1), along with the waste, a population of carefully selected bacterial strains (*Clostridium thermocellum, Clostridium thermosaccharolyticum, Coprothermobacter proteolyticus,* Bacteroides, Bifidobacterium, Lactobacillus, *Escherichia coli,* Eubacterium, Peptococcus, Enterobacter) some of which are known to be commensal for animal intestines.

In accordance with the invention, waste decomposition can be carried out at temperatures which are in the range 20° C. to 80° C. Provided that the waste is introduced into vessel (2) of the first reactor (1) without first being sterilised, it may be extremely advantageous to decompose it at a temperature in the range 45° C. to 80° C., and preferably in the range 50° C. to 70° C., to eliminate the pathogenic germs which it may contain.

In all cases, waste decomposition is carried out for a length of time which is sufficient to obtain decomposition of the proteins, polysaccharides, and lipids present in the waste to a degree of at least 80%, and preferably of over 85%. This time varies depending on the composition of the waste and the conditions under which it is decomposed (temperature, bacterial strains employed, . . . ). It is thus possible and even desirable, for each type of waste to be treated, to determine the optimum residence time for the waste in vessel (2) of the first reactor (1) by varying the operating conditions for its decomposition.

Waste decomposition results in liquefaction of the waste and its transformation into a liquid effluent composed of two phases: a liquid phase, which includes volatile fatty acids (acetic, valeric, butyric, isobutyric, propionic, caproic acid, . . . ), amines, urea, ethanol, or ammonia; and another phase which is solid, being formed by suspended particles of non decomposed matter.

Waste decomposition also results in the production of fuel gas, more particularly methane, the amount of which depends on various parameters, in particular the temperature at which waste decomposition is carried out, pH, ammonia concentration, and residence time in vessel (2) of the first reactor (1), as is conventionally the case for methane fermentation. By adjusting the parameters it is thus possible to encourage or, on the contrary, to limit production of this gas.

Once evacuated from vessel (2) of the first reactor (1), the phases of the liquid effluent resulting from waste decomposition are advantageously separated to clear the liquid phase of the suspended solid matter it contains. This liquid phase is then transferred to vessel (11) of the second reactor (10), to act as a substrate for heterotrophic or photoheterotrophic bacteria and thus to produce the biomass.

In accordance with the invention, these bacteria are advantageously selected from bacteria in the Rhodospirillaceae family, more particularly in the genera Rhodobacter and Rhodospirillum, because of their capacity, both for heterotrophy and for photoheterotrophy, to assimilate a large number of carbon-containing sources, in particular the volatile fatty acids present in the liquid phase of the effluent.

The biomass is produced at a temperature in the range about 20° C. to 30° C. and at a pH close to normal. Its yield depends on the rate of growth of the bacteria used and, for a given bacterial strain, on the conditions under which it is carried out, in particular the use or otherwise of light.

As it grows the bacteria produce a biomass which is made up of proteins, carbohydrates, lipids, and nucleic acids and which, once separated from the residual effluent in which it is immersed and once sterilised, can be used in animal feeds.

In addition to containing non decomposed organic matter, the residual solid material from decomposition is rich in organic nitrogen and phosphorous and is routed to a composting unit (20) for exploitation in the form of compost.

EXAMPLES: TREATMENT OF LIQUID MANURE ON A PIG FARM

The industrial feasibility of the waste treatment method and plant of the invention has been verified for their application to purifying liquid manure on an intensive pig farm, by extrapolating experimental results obtained for small volumes of waste and by simulating the method and the plant at an industrial scale.

This verification was carried out taking account of the operational constraints (labor time, space available for treating the liquid manure, . . . ), the cost constraints, and the hygiene constraints specific to such a farm.

The farm considered was a "Farrow-Fatten" type farm comprising 150 farrowing sows giving birth to about 2700 piglets per annum (i.e., an average of 18 piglets per sow).

Two different operating techniques (Technique 1 and Technique 2) using different variations of the plant were evaluated on the basis of an average daily liquid manure production of 10.1 m$^3$, under the following conditions and with the following results.

1) Technique 1:

Technique 1 carried out the following:

mesophilic decomposition of the liquid manure at a temperature of 30° C.;

filtering the effluent resulting from this decomposition and composting the solid material recovered during the filtration;

producing edible biomass using photoheterotrophy and anaerobiosis; and spreading the residual effluent.

a) Liquid manure decomposition:

The liquid manure was decomposed in a pit located beneath pig housing (for example, under the slats) and supplied with liquid manure under gravity. The pit was designed to have a capacity corresponding to 2 months liquid manure production, and this pit had a minimum working volume of 650 m$^3$.

The liquid manure was decomposed by the bacteria naturally present therein, at a temperature of 30° C. which, since the temperature in the housing was generally held at 20° C., was achieved by a heating means such as a coil supplied by circulating hot water and immersed in the liquid manure. The liquid manure was also decomposed at a pH in the range 5.9 to 6.8 to limit methane roduction, necessitating slight acidification of the manure which had a pH of between 7 and 7.6.

Under these conditions, the proteins, polysaccharides, and lipids initially present in the liquid manure were decomposed to a degree of over 85% in 14 days.

The effluent resulting from the decomposition was collected by emptying the pit, for example by periodic flushing with a volume and frequency (every two weeks, every month, or every two months) adjusted to the volume and frequency of the supply of liquid manure to the pit. The effluent was then supplied to a filtration unit, for example via an outflow channel.

b) Effluent filtration:

The effluent was filtered using a rotary filter 0.7 m in length, 0.5 m in width and 0.7 m high provided with 150 $\mu$m openings. This filter was supplied with effluent via an open wheel centrifugal pump at a flow rate of 1 m$^3$/hour and was rotatably driven by a variable speed geared motor. It was also equipped with a pressure washing system to prevent it from becoming clogged by the solid matter present in the effluent.

Filtration eliminated at least 60% of the solid matter suspended in the effluent, and led to the production of a volume of 1.6 m$^3$/day of filtration residue comprising 20% by weight of dry matter (i.e., a production of 320 kg of dry matter per day), thus leaving a volume of 8.5 m$^3$/day of filtered effluent.

The filtered effluent was then transferred into the compartment provided for producing the edible biomass, for example via an outflow channel, either directly or after temporary storage in an intermediate tank.

c) Edible biomass production:

The edible biomass was produced using a *Rhodobacter capsulatus* culture, carried out by photoheterotrophy and anaerobiosis in a tank designed for an effluent residence time of 7 days and thus having a working volume of 66 m$^3$.

This tank had a surface area of 22 m$^2$ and a working depth of 3 m. It was provided with artificial lighting comprising 120 150 Watt (W) neon lights in 5 rows each of 24 neon lights to produce continuous illumination with a total lighting power of 18 kW. The tank was thermally insulated and also included a continuous stirring means.

The culture temperature was 30° C. and its pH was 6.9.

Under those conditions, biomass was produced at about 0.08 g of dry matter per liter per hour, namely a biomass production of about 160 kg of dry matter per day.

The biomass produced was separated from the effluent by flotation using flotation equipment located downstream of the tank and supplied from the tank, for example via an outflow channel. The flotation equipment separated the solid matter suspended in the liquid phase (effluent) by injecting a mixture of air and water pressurised to 5–6 bars. The bubbles generated by this mixture attached themselves to the matter and brought it to the surface of the liquid phase where it could be recovered by skimming.

Flotation equipment was used having dimensions that enabled 1 m$^3$/hour of the mixture of biomass and effluent to be treated.

The concentration of the biomass recovered after flotation was in the range 30 g to 60 g of dry matter per liter. It was possible to concentrate it further by allowing it to drain for several days in a draining vessel then dehydrating it if required to exploit it in the form of a dry product.

The protein concentration of this biomass represented about 50% by weight of its dry weight and the nutritional value was at least equivalent to that of soya.

d) Composting solid matter recovered during filtration:

The filtration residue underwent accelerated composting in forced aeration silos. Since the volume of filtration residue to be composted was 1.6 m³/day (i.e., 320 kg of dry matter per day), composting was carried out using two identical corridor silos with a working capacity of 30 m³ (working height: 2 m, working width: 3 m, working length: 5 m) which were each aerated by a ventilator with a flow rate of 220 m³/hour and a pressure differential of 200 mm of water.

The residence time for the filtration residue in the silos was 60 days.

Thus a compost volume of 0.45 m³/day was produced, corresponding to a compost mass of about 460 kg/day. This compost had respective organic matter, nitrogen, and phosphorous contents of 56%, 2.2% and 3.7% by weight, and could advantageously be used as a culture support.

e) Spreading residual effluent:

Technique 1 enabled the initial loads of nitrogen and phosphorous in the liquid manure to be reduced by 68% and 69% respectively and the initial COD to be reduced by 91%.

Thus after a regulation storage period of at least four months, the residual effluent could be spread on agricultural land to act as a fertiliser.

2) Technique 2:

Technique 2 carried out the following:

mesophilic decomposition of liquid manure at a temperature of 30° C;

filtering the effluent resulting from this decomposition and composting the solid matter collected during filtration;

production of an edible biomass by heterotrophy and aerobiosis; and spreading the residual effluent.

Mesophilic decomposition of the liquid manure, filtration of the effluent resulting from that decomposition and composting of the solid matter collected during the filtration were carried out under the same conditions as those used in Technique 1.

In contrast, the edible biomass was produced using a culture of *Rhodobacter capsulatus* which was formed by heterotrophy and aerobiosis in a tank with a working volume of 70 m³, namely a surface area of 14 m² and a working depth of 5 m.

This tank was provided with an aeration system comprising a booster pump with a flow rate of 130 m³/hour connected to an oxygen supply, and diffusers located at the bottom of the tank to provide the *Rhodobacter capsulatus* culture with 117 kg per day of oxygen.

The residence time of the effluent in the tank was 7 days. The culture temperature was 30° C. and its pH was 6.9.

Under those conditions, a biomass production of about 0.05 g of dry matter per liter per hour was produced, namely a biomass production of about 100 kg of dry matter per day.

As for Technique 1, the biomass was separated from the effluent by flotation using flotation equipment located downstream of the tank and supplied from the tank. The concentration of the biomass collected after flotation was in the range 30 g to 60 g of dry matter per liter.

Technique 2 reduced the initial nitrogen and phosphorous loads in the liquid manure by 48% and 69% respectively and the initial COD was reduced by 91%. Here again, after a regulation storage period of at least four months, the residual effluent could be spread on agricultural land to act as a fertiliser.

Table 2 below illustrates the principal performances of Techniques 1 and 2.

TABLE 2

| | BIOMASS PRODUCTION kg of dry matter/m³ | COMPOST PRODUCTION kg of dry matter/m³ | PURIFYING PERFORMANCE | | |
| --- | --- | --- | --- | --- | --- |
| | | | ΔN | ΔP | ΔCOD |
| TECHNIQUE 1 | 16 | 34 | 68% | 69% | 91% |
| TECHNIQUE 2 | 10 | 34 | 48% | 69% | 91% |

The invention is not limited to the specific embodiments described above; it encompasses any variation which could be made by the skilled person without departing from the ambit and scope of the invention.

What is claimed is:

1. An open circuit method for converting organic waste into an edible biomass, comprising the steps of:
    a) collecting said organic waste;
    b) introducing said organic waste into the vessel of a first reactor without prior sterilization;
    c) decomposing said organic waste in the vessel of said first reactor by mesophilic or thermophilic anaerobic bacteria for a time sufficient to convert said organic waste into a liquid effluent containing carbonaceous and nitrogenous compounds assimilable by heterotrophic or photoheterotrophic bacteria;
    d) recovering said liquid effluent;
    e) transferring said liquid effluent to the vessel of a second reactor;
    f) culturing heterotrophic or photoheterotrophic bacteria in the vessel of said second reactor whereby an edible biomass is produced by assimilation of the carbonaceous and nitrogenous compounds present in said liquid effluent by said heterotrophic or photoheterotrophic bacteria;
    g) recovering said edible biomass; and
    h) packaging said edible biomass.

2. The method of claim 1, wherein said mesophilic or thermophilic anaerobic bacteria consist of a mixture of proteolytic, saccharolytic and cellulolytic bacteria.

3. The method of claim 1, wherein said mesophilic or thermophilic anaerobic bacteria are commensal animal intestine bacteria.

4. The method of claim 1, wherein said organic waste are decomposed by thermophilic anaerobic bacteria at a temperature in the range of 45° C. to 80° C.

5. The method of claim 1, wherein said organic waste are decomposed for a time sufficient to convert to a degree of over 80% the proteins, polysaccharides and lipids present in said organic waste into carbonaceous and nitrogenous compounds assimilable by heterotrophic or photoheterotropic bacteria.

6. The method of claim 1, wherein the recovery of said liquid effluent comprises the steps of evacuating said liquid effluent from the vessel of said first reactor and, then, removing the particles of non-decomposed organic waste which are in suspension in said liquid effluent.

7. The method of claim 6, wherein said particles of non-decomposed organic waste are removed by means of filtration or screening said liquid effluent.

8. The method of claim 7, wherein said heterotrophic or photoheterotrophic bacteria are selected from the group consisting of the Rhodospirillaceae family.

9. The method of claim 8, wherein said heterotrophic or photoheterotrophic bacteria are selected from the group consisting of bacteria of the germs Rhodobacter, bacteria of the genus Rhodospirillum, and mixtures thereof.

10. The method of claim 1, wherein said edible biomass is produced by heterotrophic bacteria under aerobic conditions.

11. The method of claim 1, wherein the recovery of said edible biomass comprises evacuating a mixture of said edible biomass and said liquid effluent from the vessel of said second reactor and, then, separating said edible biomass from said liquid effluent.

12. The method of claim 1, said edible biomass is separated from said liquid effluent by means of flotation.

13. The method of claim 1, further comprising the recovery of the fuel gas released during said step of decomposing said organic waster in a vessel of said first reactor.

14. The method of claim 13, further comprising the combustion of said fuel gas to heat the vessel of said first reactor.

15. The method of claim 6, further comprising composting said particles of non-decomposed organic waste.

16. The method of claim 1, wherein said organic water comprises animal waste.

17. The method of claim 1, wherein said organic waste comprises sludge from water purification.

* * * * *